US009574983B2

(12) United States Patent
Santner

(10) Patent No.: US 9,574,983 B2
(45) Date of Patent: Feb. 21, 2017

(54) METHOD OF DETERMINING MEASUREMENT DATA OF SAMPLES AND RHEOMETER

(71) Applicant: ANTON PAAR GMBH, Graz-Strassgang (AT)

(72) Inventor: Friedrich Santner, Seiersberg (AT)

(73) Assignee: Anton Paar GmbH, Graz-Strassgang (AT)

( * ) Notice: Subject to any disclaimer, the term of this patent is extended or adjusted under 35 U.S.C. 154(b) by 176 days.

(21) Appl. No.: 14/627,166

(22) Filed: Feb. 20, 2015

(65) Prior Publication Data

US 2015/0233807 A1 Aug. 20, 2015

(30) Foreign Application Priority Data

Feb. 20, 2014 (AT) .................................. 50128/2014

(51) Int. Cl.
*G01N 11/14* (2006.01)
*G01N 11/00* (2006.01)

(52) U.S. Cl.
CPC ............. *G01N 11/14* (2013.01); *G01N 11/142* (2013.01); *G01N 2011/0006* (2013.01)

(58) Field of Classification Search
USPC ........................................... 73/54.31, 54.28
See application file for complete search history.

(56) References Cited

U.S. PATENT DOCUMENTS

2011/0100098 A1* 5/2011 Lauger ................ G01N 11/142
73/54.28

* cited by examiner

*Primary Examiner* — Michael A Lyons
*Assistant Examiner* — Jean Morello
(74) *Attorney, Agent, or Firm* — Laurence A. Greenberg; Werner H. Stemer; Ralph E. Locher

(57) ABSTRACT

A method determines measurement data of samples by using a rotation rheometer and a linear DM(T)A analysis unit. The rotation rheometer has units for measuring and/or adjusting the normal force exerted by or on the measurement shaft and/or the speed, deflection angle and/or torque of the measurement shaft. The linear DM(T)A analysis unit has units for measuring the tensile and/or pressure force and/or the position and/or the feed movement of its adjustment rod. The sample to be examined is arranged between opposite measurement parts. Accordingly, the rotational forces or torques transmitted via the sample from the measurement shaft to the adjusting rod, when obtaining measurement data with the linear DM(T)A analysis unit, and, when obtaining measurement data by the rotation rheometer, for the tensile or pressure forces or linear adjustment forces transmitted via the sample from the adjustment rod to the measurement shaft are compensated for.

26 Claims, 2 Drawing Sheets

METHOD OF DETERMINING MEASUREMENT DATA OF SAMPLES AND RHEOMETER

CROSS-REFERENCE TO RELATED APPLICATION

This application claims the priority, under 35 U.S.C. §119, of Austrian application A50128/2014, filed Feb. 20, 2014; the prior application is herewith incorporated by reference in its entirety.

BACKGROUND OF THE INVENTION

Field of the Invention

The invention concerns a method for determining measurement data of samples according to the generic terms of the first independent claim. The invention further concerns a rheometer according to the second independent claim that is suited, in particular, to execute the method according to the invention.

Rheometers are instruments for determining the flow characteristics, in particular of viscoelastic samples. Known methods for determining flow characteristics include, e.g., rotation, creep, relaxation, and oscillation tests. Using a rheometer, solids are also examined in the oscillation test. Such tests are known as 'dynamic mechanical analyses'.

Dynamic mechanical analyses are also used to determine the viscoelastic properties of polymers and other materials. By applying various tension conditions, material properties such as the storage modulus and the loss modulus (complex modulus) can be determined as a function of temperature, frequency, and other dependent values.

In dynamic mechanical analysis (DMA), also known as dynamic mechanical thermoanalysis (DMTA), minor sinusoidal mechanical stresses are applied to a test piece. When a sample behaves in a purely elastic manner, there is no phase displacement over time between the effect of the force and the response signal. In purely viscous behavior, as occurs in 'Newtonian' fluids, a phase displacement of exactly 90° can be found. In viscoelastic samples such as polymers, a phase displacement, and thus elastic and viscous properties can be measured.

Using dynamic mechanical analysis, a very wide range of different materials with different properties can be examined. In order to cover the broadest possible range of properties, widely varying types of stress such as tension, pressure, bending, or torsion. Thus, measuring devices for materials with low modulus values, as is the case with elastomers, and high modulus values, as is the case with composite materials, can be carried out with the limiting force and distance ranges of the measurement devices.

Material samples with small cross sections are typically measured under tensile stress in order to obtain sufficient force resolution. Due to the high sensitivity and accuracy of DMTA torsion measurements, this mode is preferred for measuring thermoplastics. Due to the anisotropic properties of composite materials, they are almost exclusively analyzed in bending mode. Materials with low modulus values such as elastomers are typically measured under pressure or shearing.

SUMMARY OF THE INVENTION

The objection of the invention is to provide a method and a rheometer with which numerous different parameters can be measured on a single probe, in particular simultaneously or at close time intervals. Furthermore, such a rheometer should be simple in design, and determine the measurement values with the greatest accuracy. Additionally, ease of operation and changeover is sought.

These objections are met by a method of the aforementioned type with the characteristics in the characterizing portion of the first independent claim. According to the invention, it is provided for the rotational forces or torques transmitted via the sample from the measurement shaft of the rotation rheometer to the adjusting rod of the linear DM(T)A analysis unit, when obtaining measurement data with the linear DM(T)A analysis unit, and, when obtaining measurement data by the rotation rheometer, for the tensile or pressure forces or linear adjustment forces transmitted via the sample from the adjustment rod to the measurement shaft to be compensated during the determination and/or analysis of the measurement data.

A rheometer according to the invention is characterized by the characteristics of the characterizing portion of the second independent claim. According to the invention, it is provided for the rheometer to contain at least one compensation unit, by which rotational forces or torques transmitted via the sample from the measurement shaft of the rotation rheometer to the adjusting rod of the linear DM(T)A analysis unit, when obtaining measurement data with the linear DM(T)A analysis unit, and, when obtaining measurement data by the rotation rheometer, for the tensile or pressure forces or linear adjustment forces transmitted via the sample from the adjustment rod to the measurement shaft to be compensated during the determination and/or analysis of the measurement data.

According to the invention, thus, a combination of a rotation rheometer with integrated torque measurement and, if applicable, normal force measurement having a linear DM(T)A analysis unit with a linear motor with integrated force measurement is provided. The rotation rheometer according to the invention may be modular in structure, whereby the rheometer and the DM(T)A analysis unit can be arranged so as to be modularly interchangeable in the frame or housing of the rheometer. According to the invention, it is possible to determine the complex modulus of rigidity and the complex elasticity modulus, as well as the transverse contraction of a sample as a function of temperature and humidity, on a single sample, in particular simultaneously, within a measurement process. The modulus of rigidity and the elasticity modulus can thus be determined under identical conditions as a function of temperature and/or frequency and/or amplitude of the oscillation without irreversible effects of the sample compromising the measurement. Structure modifications to the sample due to experimental conditions are thus identical for both measurements. This also allows for the determination of Poisson's ratio in a single measurement, simultaneously or in immediately consecutive measurements, on the same sample, with alternation between torsion and tension or pressure measurements. This process is made possible with maximum accuracy by compensating the mutual forces of the rotation rheometer and the linear DM(T)A analysis unit.

It is also possible for the rotation rheometer or the DM(T)A analysis unit to be incorporated in the top or bottom of the rheometer, as desired. Additionally, errors in measuring the parameters are minimized because all measurements can either be carried out simultaneously or immediately consecutively on a single sample, and changes to the sample over short periods of time are negligible or nonexistent.

In a known option for determining Poisson's ratio, cylindrical samples are stimulated in uniaxial frequencies, and the amplitudes of the axial and lateral elongation and their phase displacement are measured. The difficulty is measuring the lateral elongation using touch-free sensors and determining the phase displacement. Because the phase displacement is very small and directly related to Poisson's ratio, the error for such measurements is substantial. For this reason, samples with small phase angles cannot be measured with this method.

Another known method for measuring Poisson's ratio is based on secondary effects, e.g., measuring the complex modulus and the dynamic stiffness. The geometry factor of the sample has a significant influence on the result of this method. Due to inadequate information on this geometry factor, however, this method is severely limited. Another known secondary method is measuring the propagation of waves in the axial direction in rod samples. This method is severely limited in terms of frequency range.

Another option for determining Poisson's ratio is that of measuring two modulus values. It is known that different modulus values, e.g., the complex shear modulus and the complex elasticity modulus, are related to Poisson's ratio; in the case of the shear modulus and the elasticity modulus, this relation is expressed by the following formula:

$$v = \frac{E}{2*G} - 1$$

The complex modulus values are typically determined using a dynamic mechanical analysis. After carrying out the individual measurements (determining E and G), Poisson's ratio can be determined. Because each measurement must be taken individually, and the device must be reconfigured, or another device must be used, these measurements are very effort-intensive. Another disadvantage of this method is that the determination cannot be carried out using a single sample. The resultant error effect due to samples that are not exactly homogeneous and of equal dimensions significantly influences the resultant Poisson's ratio. Additionally, the high material consumption resulting from the use of at least two samples is highly disadvantageous in settings of low material availability, as is frequently the case in synthetic chemistry. Moreover, changes to the sample occur between measurements. According to the invention, these disadvantages are avoided by simultaneous measurement—or measurement at close intervals—of the same sample, thus making an exact determination of Poisson's ratio.

Additional advantages of the invention are that a greater range of movement of the adjustment rod is possible with the linear motor used, because measurements with the DMTA analysis unit and the rotation rheometer can be carried out independently, and there is no limitation caused by torque measurements.

Additional problems are eliminated by the invention, i.e., the fact that the adjustment of the adjustment rod of the linear motor affects the position of the measurement shaft or the vertical position of the measurement shaft of the rotation rheometer, which may cause errors, as well as the fact that the rotation of the measurement motor of the rotation rheometer that drives the measurement shaft drives the adjustment rod of the linear motor of the DM(T)A analysis unit—via the sample—to a rotational movement, which would be followed by the adjustment rod of the linear motor because the adjustment rod of the linear motor is only rigidly mounted in the longitudinal direction. The essential objective of the invention, to eliminate the mutual influence of the rotation rheometer and the linear DM(T)A analysis unit in order to obtain exact readings, is attained according to the invention by the aforementioned characteristics of the independent claims. This process significantly increases the sensitivity of the rheometer according to the invention, or makes the readings obtained available at the highest accuracy.

Generally, it should be noted that the rotation rheometer used according to the invention has the usual/known diverse structure of known rotation rheometers, i.e., it also has a measurement or drive motor that drives a measurement shaft mounted on highly precise air bearings with specified torques, speeds, or oscillations. Much the same applies to the linear DM(T)A analysis unit used according to the invention, which may also have all characteristics known from the prior art for such analysis units. It is essential to the invention for both devices, i.e., a rotation rheometer and a linear DM(T)A analysis unit to be combined into a shared rheometer in order to obtain the benefits of the invention.

Advantageously, the method according to the invention is carried out such that, during the determination of the measurement data, the rotation rheometer and the DM(T)A analysis unit are started together, and the measurement data of the sample are obtained with the rotation rheometer and the DM(T)A analysis unit either alternating one immediately after the other or simultaneously. In particular, this process avoids changes to the sample during immediately consecutive measurements. Simultaneous measurement determines Poisson's ratio with the greatest accuracy.

If measurement data are obtained with the rotation rheometer simultaneously with the DM(T)A analysis unit, it is advantageous for the effects of the adjustment rod on the measurement shaft in the direction of the feed axis of the adjustment rod during the determination of the measurement data with the rotation rheometer to be compensated by maintaining the measurement shaft and/or the measurement component supported by the measurement shaft to be kept at a constant height relative to a reference point determined on the rotation rheometer, preferably by stiffening the bearing or exerting a counterforce, or for the linear adjustment forces and resultant movements exerted on the measurement component of the adjustment rod to be compensated mathematically during the analysis of the measurement data.

It is simple during the determination of the measurement data with the DM(T)A analysis unit to compensate the effects of the torques exerted by the measurement shaft on the adjustment rod by keeping the adjustment rod and/or measurement part rotationally invariant, preferably by stiffening the bearing or exerting a counter force, or by mathematically compensating for the rotational forces exerted on the measurement part by the measurement shaft and the resultant movements during the analysis of the measurement data.

Because forces or torques are not always exerted in the same direction of movement, and periodic forces or oscillating forces frequently occur, according to the invention, it may be provided for periodic movements, in particular oscillations, and/or periodic, in particular oscillating, forces of the adjustment rod and/or the measurement shaft to be compensated with counter movements and/or counter forces occurring at the same intervals.

To compensate for the forces exerted on the linear DM(T)A analysis unit by the rotation rheometer, and vice versa, it may be provided for the measurement part supported by the adjustment rod and the measurement shaft to abut one another without pressure or at a specified pressure, and the specified linear movements of the adjustment rod and/or rotational movements of the measurement shaft necessary for the measurements to be carried out, and the forces, pressures, or torques occurring between the measurement shaft and the adjustment rod and vice versa, and the resultant movements and/or changes in movement to be recorded and made available for calibrations during the determination of the measurement data for mathematical compensation, preferably in the form of calibration tables. With the calibration tables obtained, the readings obtained during the measurement may be linked or converted, and are thus available as exact readings. These calibration values may be combined with the compensation based on readings obtained with sensors.

It is advantageous in particular for rapid determination of measurement data if, during the determination of the measurement data, the forces exerted by the adjustment rod via the sample on the measurement shaft, and vice versa, and the resultant movements and/or changes in movement to be continuously sensed and determined, and used for the immediate exertion of counter forces, counter torques, and/or for the induction of counter movements on the adjustment rod and/or the measurement shaft to compensate the forces and movements and/or changes in movement of the adjustment rod and/or the measurement shaft. With sensors that react at the appropriate speed and accuracy, it is possible to sense forces, torques, and/or linear movements and to induce the corresponding counter movements or the exertion of the corresponding counter forces.

The reaction to mutual influences of the rheometer and the DM(T)A analysis unit may be eliminated or avoided by adjusting or increasing the stiffness of the bearing of the measurement shaft relative to a height adjustment relative to the base and/or by adjusting or increasing the stiffness of the bearing of the measurement rod relative to a rotation around its feed axis. It may also be provided that, to compensate for the forces exerted by the adjustment rod, the height of the measurement part supported by the measurement shaft to be kept at a specified level or specified distance from the base relative to a base specified on the rotation rheometer. This compensation is particularly simple to implement.

In practice, it has been found to be simple and useful for compensation if the adjustment forces exerted by the adjustment rod on the measurement shaft to be determined by the unit normal force measurement unit provided in the rotation rheometer, and for these readings to be provided to a compensation unit to adjust the height of the measurement shaft or the measurement part an adjustment unit adjusting the height of the measurement shaft, and/or for the DM(T)A analysis unit to comprise a compensation unit controlling a unit that rotates the adjustment rod and turns it depending on a sensor that determines the rotational position of the adjustment rod.

For compensation, it may also be provided for the measurement shaft with the measurement part and any measurement motor driving the measurement shaft to be mounted together on a support opposite the specified base on the rheometer with an adjustment drive so as to allow for height adjustments, and for the adjustment drive to be provided with adjustment signals depending on the pressure forces exerted by the adjustment rod on the measurement shaft, thus adjusting the height of the support.

Good compensation and exact measurement results become possible if the DM(T)A analysis unit to be rotatably mounted relative to the base about the adjustment axis of the adjustment rod with a rotation drive, and for the compensation unit to control the rotation drive, and for the DM(T)A analysis unit, depending on the rotational forces exerted by the measurement shaft on the adjustment rod, to rotate the DM(T)A analysis device in order to compensate for these forces or torques.

In the rheometer according to the invention, it is advantageous for the torques and pressure forces to be compensable simultaneously with the compensation unit in the case of simultaneous determination of measurement data with the rotation rheometer and the DM(T)A analysis unit. This makes it simple to obtain measurement data simultaneously with the rotation rheometer and the linear DM(T)A analysis unit from the same sample without unnecessary time consumption.

In structural terms, it is simple and advantageous for operation if the compensation unit has or controls mechanical, electrical, or pneumatic adjustment units or engines with which the torques exerted by the measurement shaft on the adjustment rod can be compensated by keeping the adjustment rod in an unvarying rotational position in its bearing or counteracting its rotation by stiffening the bearing.

A simple structure and good control can be obtained if the compensation unit has or controls mechanical, electrical, or pneumatic adjustment units or engines with which the pressure forces exerted by the adjustment rod on the measurement shaft can be compensated by keeping the measurement shaft at a constant height or by counteracting height adjustment.

In order to absorb the forces exerted by the rotation rheometer on the DM(T)A analysis unit and vice versa, it is useful for the compensation units to have sensor units, whereby the sensor unit senses the forces or torques exerted by the adjustment rod on the measurement shaft and by the measurement shaft on the adjustment rod and controls the adjustment units or engines to compensate the movements initiated by pressure forces and torques.

To evaluate the measurement data and compensate the mutual influence, it is advantageous for the compensation units to be associated with at least one memory for calibration values determined for the force exerted by the measurement shaft on the adjustment rod and vice versa in the case of direct mutual abutment of the respective measurement parts and application of specified, customary force and/or torque and/or adjustment values for measurements, and for the control of the adjustment units or engines during measurements on a sample to take into account the stored calibration values and the actual readings determined during the measurements.

Exact operation and readings are obtainable if the measurement shaft of the rotation rheometer is rigidly mounted with an air bearing relative to a movement in the direction of feed of the adjustment rod or the rheometer axis, and/or the adjustment rod is rigidly mounted with an air bearing relative to a rotation around its adjustment axis the adjustment units or engines are arranged to regulate the air supply to the respective bearing and/or to change the geometry of the bearing gap and/or the size of the area of the adjustment rod to which air is applied or the normal distance from this area to the feed axis and/or to adjust the width of the gap between the air-supplying and the air-receiving surface and/or to adjust the fluid flowing into the respective air bearing.

It can be particularly advantageous for the adjustment rod and/or the measurement shaft to be mounted in an electromagnetic bearing, and for a control current regulator for the coil of the bearing to be provided as the adjustment device or engine to adjust the rigidity of the respective bearing.

Compensation is simple if a height adjustment unit is provided as an engine, with which the measurement part of the rotation rheometer and its measurement shaft and any driving measurement motor to be kept at a specified or adjustable level relative to a base specified on the rheometer, and for this height adjustment unit to be controllable and adjustable in height by the compensation unit in order to compensate for the pressure forces exerted by the adjustment rod on the measurement shaft.

It is also possible for a normal force adjustment unit for the rotation rheometer that receives measurement signals from the normal force measurement unit on the pressure forces exerted by the adjustment rod on the measurement shaft to be controlled by the compensation unit, providing the values obtained to the normal force adjustment unit in order to compensate the pressure forces.

Exact compensation is possible if a rotation drive with which the DM(T)A analysis device and/or the adjustment rod can be rotated about the adjustment axis of the adjustment rod relative to the base of the rheometer can be controlled with the compensation unit as an engine, and for the compensation unit to control the rotation drive depending on the torque exerted by the measurement shaft on the adjustment rod in order to compensate for this force, thus rotating the linear DM(T)A analysis device and/or the adjustment rod.

For the structure of the rheometer according to the invention, it is advantageous for the rotational axis of the measurement shaft and the feed axis of the adjustment rod to coincide, and/or for the compensation unit of the rotation rheometer and the compensation unit of the DM(T)A analysis unit to be combined into a shared control unit to which a computer and/or analysis unit for the readings obtained may be connected.

Other features which are considered as characteristic for the invention are set forth in the appended claims.

Although the invention is illustrated and described herein as embodied in a method for determining measurement data of samples and a rheometer, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
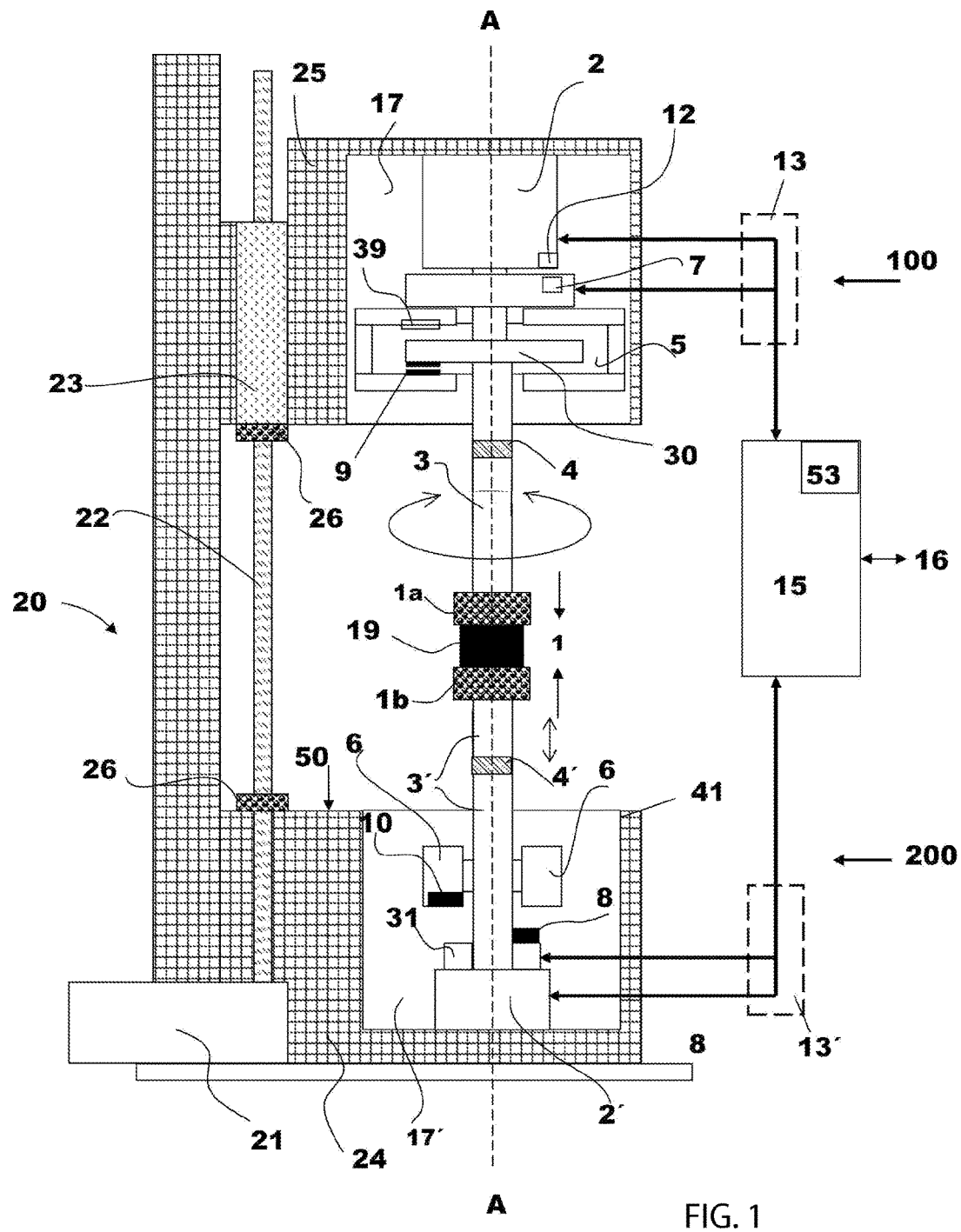
FIG. 1 is a schematic representation of a rheometer according to the invention.

Referring now to the figures of the drawings in detail and first, particularly to FIG. 1 thereof, there is shown a rheometer which contains two, preferably modularly structured and thus interchangeable units, mounted on a tripod 20 with a frame 24 and a support 25, of which the upper unit consists of a rotation rheometer 100 and the lower unit consists of a linear DM(T)A analysis unit 200. It is also possible for the linear DM(T)A analysis 200 unit to be incorporated in the top and the rotation rheometer 100 on the bottom, near the frame.

The rotation rheometer 100 contains the support 25 with a measurement motor area 17, in which a measurement or drive motor 2 is arranged that drives a measurement shaft 3 mounted in a rotary air bearing 5. The rotary air bearing 5 supports and centers the measurement shaft 3 or a bearing plate 30 connected with it. Alternative bearing options, e.g., magnetic bearings, may also be used. A measurement part 1a can be connected with the measurement shaft 3 via a coupling 4.

The support 25 is mounted in a height-adjustable manner via a control device 23 on a wrenching spindle 22. The wrenching spindle 22 is driven by a servomotor 21, and the height of the support 25 relative to a base 50 specified on the frame 24 and/or the adjustment path of the support 25 may be measured by a path measuring unit 26.

Generally, any pneumatic, hydraulic, piezoelectric, or electromechanical height adjustment of the support 25 is possible, and the vertical position of the support 25 may be determined optically, mechanically, or electrically.

The rotation rheometer 100 advantageously has a normal force measurement unit 9 on the measurement shaft 3 and/or the bearing plate 30 and/or in the bearing 5, with which forces exerted on the measurement shaft 30 in the direction of the axis A-A of the rheometer 100 can be determined. At the same time, the normal force measurement unit 9 may be structured so as to exert forces in the direction of the axis A-A on the bearing plate 30 and/or the measurement shaft 3. Alternatively or additionally to the normal force measurement unit 9, a height measurement unit 39 may be provided as a sensor for the vertical position or change in height of the measurement shaft 3 and/or the bearing plate 30. Any adjustment units may be controlled with the force measurement unit 9 and/or the height measurement unit 39, and these can be used to counteract the forces exerted on the measurement shaft 3 in the direction of the axis A-A, and to keep the vertical position of the measurement part 1a constant. Such adjustment units may operate mechanically, pneumatically, hydraulically, electrically, piezoelectrically, or electromechanically. Such an adjustment unit may be incorporated, e.g., into the normal force measurement unit 9, or be in the form of the servomotor 21 driving the wrenching spindle 22, which receives adjustment signals from the height measurement unit 39.

The drive or measurement motor 2 has a torque detector 12 with which the torque exerted by or on it may be determined. Alternatively, the torque may be determined based on the current consumption of the measurement motor. Additionally, an angle encoder 7 is provided for the measurement shaft 3, with which the angle of rotation of the measurement shaft 3 can be determined, or turning of the measurement shaft 3 can be detected. The torque and/or angle of rotation and/or the normal force present are the significant readings for a rotation rheometer 100.

A measurement part 1b opposite the measurement part 1a is supported by a linearly movable adjustment rod 3' or a lever of the DM(T)A analysis unit 200 arranged opposite the rotation rheometer 100. The measurement parts 1a and 1b delimit a gap 1 in that the sample 19 to be examined is arranged. The measurement part 1a can be interchangeably connected with the linear motor 2' via a coupling 4'. The linear motor 2' adjusts the adjustment rod 3' mounted in an air bearing 6 in the direction of the rheometer axis A-A. A path encoder 8 is associated with the adjustment rod 3' to measure the adjustment path. The measurement of the pressure or tensile forces exerted by the adjustment rod 3' can be carried out using the normal force measurement unit 9 or with dedicated force measurement units. Preferably, the linear or adjustment motor 2' is a measurement motor, and the tensile or pressure force can be determined by the power consumption of the linear motor 2'. To determine any rotation of the adjustment rod 3' about the axis A-A, angle encoder 10 may be provided that controls a rotary unit 31 to rotate the adjustment rod 3'.

During the measurements for determining the parameters of samples 19, in particular with viscoelastic behavior, an adjustment movement of the adjustment rod 3' of the linear DM(T)A analysis unit 200 causes lifting or lowering of the measurement shaft 3 or the bearing pate 30 depending on the tension or pressure exerted on the sample 19. However, the measurement shaft 3 is not sufficiently rigidly mounted to withstand such lifting or lowering, thus causing inaccuracies in the measurements. For this reason, compensation for the adjustment forces exerted by the linear motor 2' via the adjustment rod 3' and the sample 19 on the measurement shaft 3 or the bearing plate 30 is required, by means of exerting counter forces on the measurement shaft 3.

In the event of a rotation of the measurement part 1a, the rotation acts via the sample 19 on the measurement part 1b, and thus on the adjustment rod 3'. In order to counteract rotation of the adjustment rod 3' caused by this torque, the adjustment rod 3' is associated with a torque or rotation director, preferably an angle encoder 10, and is rotated or receives torque from a rotation unit 31 controlled by the angle encoder 10 in the opposite direction, running counter to the torque exerted by the measurement shaft 3. The detectors may be optical, electronic, or electromechanical in structure. The rotation unit may operate mechanically, electromechanically, electrically, pneumatically, or hydraulically.

In this way, the adjustment rod 3' is kept in a constant rotational position, and the measurement shaft 3 is kept at a constant vertical position.

The respective forces exerted by the rotation rheometer 100 on the linear DM(T)A analysis unit 200 and vice versa are thus determined by sensors, and corresponding engines, i.e., torque transmitters or linear adjustment elements are controlled in order to counteract these forces, which occur, in particular, during simultaneous measurement of a sample by the rotation rheometer 100 and the linear DM(T)A analysis unit 200. The necessary sensors and adjustment units are part of compensation units 13, 13' that are provided for the rotation rheometer 100 and the linear DM(T)A analysis unit 200 and that detect sensors and control adjustment units. Any forces or torques and adjustment movements are detected online and immediately counteracted.

It is advantageous if the compensation units 13, 13' are actuated or controlled by a superior control and regulator unit 15 that can also serve as a computer or analysis unit and as a user interface.

It may be provided for periodic movements, in particular oscillations, and/or periodic, in particular oscillating, forces of the adjustment rod 3' and the measurement shaft 3 on one another are immediately compensated for with counter movements and/or counter forces occurring at the same intervals.

To compensate the forces, adjustment movements, and torques, it may be provided for calibration purposes for the measurement parts 1a, 1b supported by the adjustment rod 3' and the measurement shaft 3 to be made to abut one another without pressure or at a specified pressure, and for the specified linear movements of the adjustment rod 3' and/or the rotational movements of the measurement shaft 3 necessary for the measurements to be carried out. The forces, pressures, or torques exerted between the measurement shaft 3 and the adjustment rod 3' and vice versa, and the resultant forces, torques, and movements and/or changes in movement are recorded as calibration values, preferably in the form of calibration tables, and made available for mathematical compensation of the measurement data during the determination of the measurement data. A memory 53 may be provided in the control unit 15 for the calibration values.

The compensation units 13, 13' contains mechanical, electrical, hydraulic, or pneumatic adjustment units or engines, e.g., the normal force measurement unit 9, the rotation unit 31, or the height adjustment unit 21, 22, which are controlled by the sensor units, e.g., the normal force measurement unit 9, the angle encoder 7, the height measurement unit 39, or the angle encoder 10. The sensor units sense the torques and adjustment forces exerted by the measurement shaft 3 on the adjustment rod 3' and by the adjustment rod 3' on the measurement shaft 3, and the adjustment units initiate the required compensations. The adjustment units may be, e.g., piezoelectric, electromagnetic, mechanical, hydraulic, or pneumatic engines. In particular, optical and/or electrical, e.g., capacitive or inductive, sensor units may be used.

When the measurement shaft 3 and the adjustment rod 3' are arranged in air bearings 5, 6, it is useful for the measurement shaft 3 to be rigidly mounted with an air bearing 5 relative to movement in the direction of the axis A-A, and/or for the adjustment rod 3' to be rigidly mounted with an air bearing 6 relative to rotation about the axis A-A. To this end, adjustment units or engines may regulate the air supply to the respective bearing and/or modify the geometry of the gap and/or the size of the air receiving surface of the adjustment rod 3' or the normal distance between this surface and the axis A-A, and/or adjust the width of the gap between the air-supplying and air-receiving surface, and/or change the pressure and amount of the fluid flowing into the respective air bearing. Such an option is shown in FIG. 2.

Another option is for the adjustment rod 3' and/or the measurement shaft 3 to be mounted in an electromagnetic bearing, and a control current regulator for the respective plunging coil to be provided as an adjustment unit or engine to regulate the rigidity of the respective bearing that is controlled by the force and/or path sensors sensing the measurement shaft 3 and/or the adjustment rod 3'.

A simple height adjustment of the rotation rheometer 100 with the measurement shaft 3 is obtained if a height adjustment unit is provided as an engine that contains the torque motor 21 and the spindle 22, and with which the support 25 and/or the measurement part 1a of the rotation rheometer 100 and the measurement shaft 3 and, if applicable, the driving measurement motor 2 are kept at a specified vertical position or an adjustable level relative to a specified base 50 on the rotation rheometer 100. This height adjustment unit can be controlled by the compensation unit 13 to compensate for the pressure forces exerted by the adjustment rod 3' on the measurement shaft 3 depending on signals of the height measurement unit 39.

The compensation unit 13 may control a normal force adjustment unit, i.e., for the forces keeping the rheometer at a specified height, depending on the measurement signals of the normal force measurement unit 9 concerning pressure forces exerted on the measurement shaft 3 by the adjustment rod 3'. The compensation unit 13 controls the normal force adjustment unit using any calibration values.

A rotary drive 31 may be provided as an engine for the rotational position of the adjustment rod 3', with which the entire DM(T)A analysis unit 200 can be rotated with the adjustment rod 3' relative to the base 50 of the rheometer 100 about the adjustment axis of the adjustment rod 3', i.e., the rheometer axis A-A. The compensation unit 13' controls the rotary drive depending on the torque exerted by the measurement shaft 3 on the adjustment rod 3' in order to compensate for this force and turns the linear DM(T)A analysis device 200.

By such means, it is simple to compensate for the influence of the torque of the rotation rheometer 100 on the linear measurement motor 2' or the adjustment rod 3' of the DM(T)A analysis unit 200 and the influence of the force exerted by the linear measurement motor 2' on the drive or measurement motor 2 of the rheometer 100.

The use of magnetic bearings for the measurement shaft 3 and the adjustment rod 3' is also possible, and they may be influenced by a power regulator.

The rheometer according to the invention also compensates for periodic adjustment movements, e.g., sinus oscillations applied by the adjustment motor 2' to the sample 19 that are transmitted to the rotation rheometer 100 or its measurement shaft 3.

The rotation rheometer 100 and the linear DM(T)A analysis unit 200 may be simultaneously started up and simultaneously obtain measurement data from the sample 19, but may also be started up immediately consecutively and obtain measurement data from the same sample 19 in immediately consecutive time frames.

Any torque requiring compensation may easily be 300 mNm. The frequencies of adjustment movements may be 50 Hz or more. The linear forces may be 50 N or more.

Figure 2A:
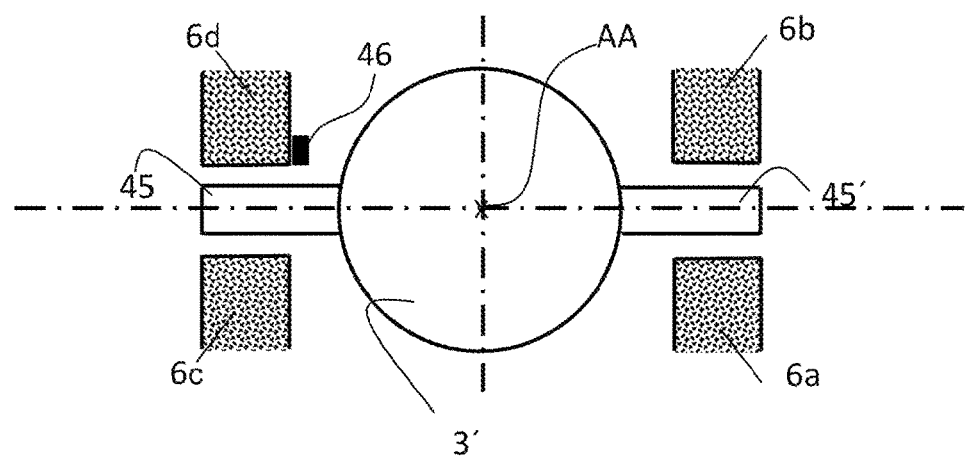
FIG. 2A is a diagrammatic, top view of an example of a compensation option.
Figure 2B:
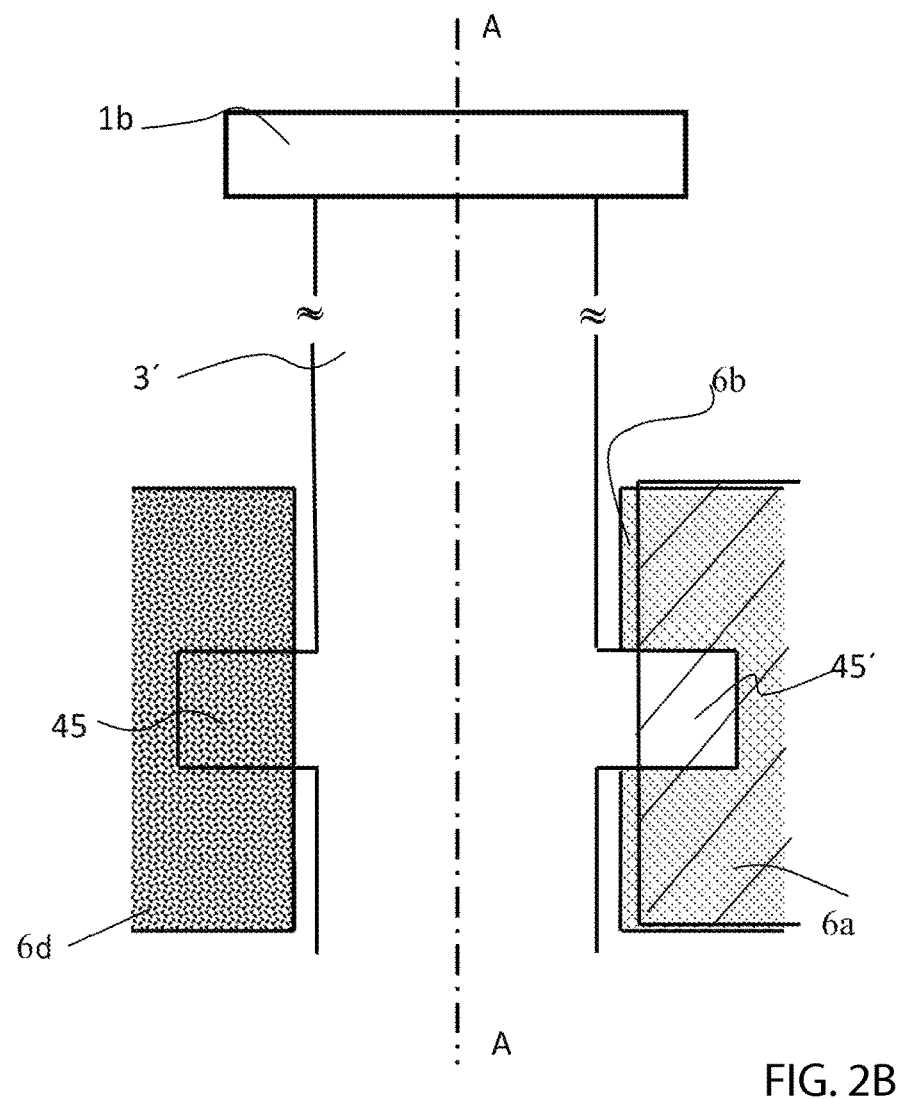
FIG. 2B is a diagrammatic, cross-sectional view of the compensation option.

FIGS. 2A and 2B are schematic representations of an air bearing 6 for the adjustment rod 3' of the linear DM(T)A analysis unit 200. Wings 45, 45' which may in particular receive air jets or piezoelectric, hydraulic, or electromagnetic forces, are attached to the adjustment rod 3'. If the application of force to the wings 45, 45' by the bearing blocks 6a and 6d or 6b and 6c is changed, the wings 45, 45' and the adjustment rod 3' rotate in the direction of greatest force. Thus, the torques applied to the adjustment rod 3' may be counteracted. A sensor 46 senses the position and/or movement of the wings 45, 45', and the adjustment unit of the compensation unit 13' controls the force or air jets.

In the case described, the wings 45, 45' are subjected to air jets. The adjustment rod 3' and its wings 45, 45' are mounted so as to be movable in the direction of the axis AA. The wings 45, 45' are between porous bearing blocks 6a, 6b, 6c, 6d from which adjustable-strength air jets are directed at the wings 45, 45'.

The invention claimed is:

1. A method for determining measurement data of samples, which comprises the steps of:
providing a rotation rheometer and a linear DM(T)A analysis unit, the rotation rheometer having units for measuring and/or adjusting a normal force exerted by or on a measurement shaft and at least one of a speed, a deflection angle or a torque of the measurement shaft, the linear DM(T)A analysis unit having an adjustment rod and units for measuring at least one of a tensile force, a pressure force, a position or a feed movement of the adjustment rod, the measurement shaft of the rotation rheometer being rotatably mounted in a bearing, and the adjustment rod of the linear DM(T)A analysis unit being linearly movably mounted in a further bearing;
disposing a sample to be examined between opposite measurement parts including a first measurement part supported by the measurement shaft and a second measurement part supported by the adjustment rod; and
compensating for rotational forces or torques transmitted via the sample from the measurement shaft of the rotation rheometer to the adjusting rod of the linear DM(T)A analysis unit, when obtaining measurement data with the linear DM(T)A analysis unit, and, when obtaining measurement data by the rotation rheometer, for the tensile force, the pressure force or linear adjustment forces transmitted via the sample from the adjustment rod to the measurement shaft during a determination and/or analysis of the measurement data.

2. The method according to claim 1, which further comprises during the determination of the measurement data, the rotation rheometer and the DM(T)A analysis unit are started together, and the measurement data of the sample are obtained with the rotation rheometer and the DM(T)A analysis unit either alternating one immediately after the other or simultaneously.

3. The method according to claim 1, wherein if the measurement data are obtained with the rotation rheometer effects of the adjustment rod on the measurement shaft in a direction of a feed axis of the adjustment rod are compensated for by maintaining the measurement shaft and/or the measurement component supported by the measurement shaft is kept at a constant height relative to a reference point determined on the rotation rheometer, or for the linear adjustment forces and resultant movements exerted on the measurement component of the adjustment rod are compensated mathematically during the analysis of the measurement data.

4. The method according to claim 1, wherein during the determination of the measurement data with the DM(T)A analysis unit effects of the torques exerted by the measurement shaft on the adjustment rod are compensated for by keeping the adjustment rod and/or the measurement part rotationally invariant, or by mathematically compensating for the rotational forces exerted on the measurement part by the measurement shaft and resultant movements during the analysis of the measurement data.

5. The method according to claim 1, which further comprises compensating for at least one of periodic movements or periodic forces of the adjustment rod and the measurement shaft on one another with at least one of counter movements or counter forces occurring at same intervals.

6. The method according to claim 1, wherein the measurement part supported by the adjustment rod and the measurement shaft abut one another without pressure or at a specified pressure, and specified linear movements of the adjustment rod and/or rotational movements of the measurement shaft necessary for measurements to be carried out, and the forces, the pressures, or the torques occurring between the measurement shaft and the adjustment rod and vice versa, and resultant movements and/or changes in movement are recorded and made available for calibrations during the determination of the measurement data for mathematical compensation.

7. The method according to claim 1, wherein during the determination of the measurement data, the forces exerted by the adjustment rod via the sample on the measurement shaft, and vice versa, and resultant movements and/or changes in movement are continuously sensed and determined, and used for an immediate exertion of counter forces, counter torques, and/or the induction of counter movements on the adjustment rod and/or the measurement shaft compensate the forces and movements and/or changes in movement of the adjustment rod and/or the measurement shaft.

8. The method according to claim 1, wherein a stiffness of the bearing of the measurement shaft is increased or adjusted relative to a height adjustment relative to a base and/or by adjusting or increasing a stiffness of the further bearing of the adjustment rod relative to a rotation around a feed axis in order to compensate.

9. The method according to claim 1, wherein to compensate for the forces exerted by the adjustment rod, a height of the measurement part supported by the measurement shaft is kept at a specified level or specified distance from a base relative to the base specified on the rotation rheometer.

10. The method according to claim 1, which further comprises:
determining adjustment forces exerted by the adjustment rod on the measurement shaft via a normal force measurement unit provided in the rotation rheometer and for readings of the adjustment forces to be provided to a compensation unit to adjust a height of the measurement shaft or the measurement part, an adjustment unit and/or the DM(T)A analysis unit contains a further compensation unit controlling a unit that rotates the adjustment rod and turns the adjustment rod depending on signals provided by a sensor that determines a rotational position of the adjustment rod.

11. The method according to claim 1, wherein the measurement shaft with the measurement part and any measurement motor driving the measurement shaft are mounted together on a support opposite a specified base on the rheometer with an adjustment drive so as to allow for height adjustments, and the adjustment drive is provided with adjustment signals depending on the pressure forces exerted by the adjustment rod on the measurement shaft, thus adjusting the height of the support.

12. The method according to claim 1, wherein the DM(T)A analysis unit is rotatably mounted relative to a base about an adjustment axis of the adjustment rod with a rotation drive, a compensation unit controls the rotation drive, and the DM(T)A analysis unit, depending on the rotational forces exerted by the measurement shaft on the adjustment rod, rotates the DM(T)A analysis device in order to compensate for the forces or the torques.

13. A rheometer for determining rheometric measurement data, the rheometer comprising:
a rotation rheometer having a bearing, a measurement part, a measurement shaft and units for at least one of measuring normal forces, adjusting the normal forces, measuring a speed of said measurement part, measuring a torque exerted by said measurement shaft or on said measurement shaft, or measuring an angle of deflection of said measurement shaft, said measurement shaft is rotatably mounted in said bearing;
a linear DM(T)A analysis unit having an adjustment rod, a further measurement part, a further bearing, a linearly adjustable adjustment rod guided in said further bearing, and units for at least one of measuring tensile forces, measuring pressure forces, determining a position of said adjustment rod, and determining a feed movement of said adjustment rod, said further measurement part and said measurement part forming a measurement gap and a sample to be examined is inserted into said measurement gap; and
at least one compensation unit, by which rotational forces or torques transmitted via the sample from said measurement shaft of said rotation rheometer to said adjustment rod of said linear DM(T)A analysis unit, and when obtaining measurement data with said linear DM(T)A analysis unit, and, when obtaining measurement data by said rotation rheometer, the tensile forces, the pressure forces or linear adjustment forces transmitted via the sample from said adjustment rod to said measurement shaft are compensated during a determination and/or analysis of the measurement data.

14. The rheometer according to claim 13, wherein the torques and the pressure forces are compensable simultaneously with said compensation unit in a case of simultaneous determination of the measurement data with said rotation rheometer and said DM(T)A analysis unit.

15. The rheometer according to claim 13, wherein said compensation unit has or controls mechanical, electrical, or pneumatic adjustment units or engines with which the torques exerted by said measurement shaft on said adjustment rod can be compensated by keeping said adjustment rod in an unvarying rotational position in said further bearing or counteracting its rotation by stiffening said further bearing.

16. The rheometer according to claim 13, wherein said compensation unit has or controls mechanical, electrical, or pneumatic adjustment units or engines with which the pressure forces exerted by said adjustment rod on said measurement shaft can be compensated by keeping said measurement shaft at a constant height or by counteracting height adjustment.

17. The rheometer according to claim 16, wherein said compensation unit is one of a plurality of compensation units having sensor units, whereby said sensor units sense the pressure forces or the torques exerted by said adjustment rod on said measurement shaft and by said measurement shaft on said adjustment rod and controls said adjustment units or said engines to compensate the movements initiated by the pressure forces and the torques.

18. The rheometer according to claim 16,
further comprising at least one memory; and
wherein said compensation unit is one of a plurality of compensation units connected to said at least one memory for calibration values determined for a force exerted by said measurement shaft on said adjustment rod and vice versa in a case of direct mutual abutment of said further measurement part and said measurement parts and application of specified, customary force and/or torque and/or adjustment values for measurements, and for a control of said adjustment units or said engines during measurements on the sample to take into account stored calibration values and actual readings determined during the measurements.

19. The rheometer according to claim 16, wherein said measurement shaft is rigidly mounted with said bearing being an air bearing relative to a movement in a direction of a feed axis or rheometer axis, and/or said adjustment rod is rigidly mounted with said further bearing being a further air bearing relative to a rotation around an adjustment axis, said adjustment units or said engines are disposed to regulate an air supply to said air bearing and said further air bearing and/or to change a geometry of a bearing gap and/or a size of an area of said adjustment rod to which air is applied or a normal distance from the area to the feed axis and/or to adjust a width of a gap between an air-supplying and an air-receiving surface and/or to adjust a fluid flowing into said air bearing or said further air bearing.

20. The rheometer according to claim 13,
further comprising a control current regulator; and
at least one of said bearing and said further bearing is an electromagnetic bearing with coils, at least one of said adjustment rod or said measurement shaft is mounted in said electromagnetic bearing, and said control current regulator for said coils is provided as an adjustment device or an engine to adjust a rigidity of said electromagnetic bearing.

21. The rheometer according to claim 13, further comprising:
a base; and
a height adjustment unit functioning as an engine, with said height adjustment unit said measurement part of said rotation rheometer and said measurement shaft and any driving measurement motor are kept at a specified or adjustable level relative to said base specified on the rheometer, and said height adjustment unit is controllable and adjustable in height by said compensation unit for compensating for the pressure forces exerted by said adjustment rod on said measurement shaft.

22. The rheometer according to claim 13, further comprising:
a normal force measurement unit; and
a normal force adjustment unit for said rotation rheometer and receiving measurement signals from said normal force measurement unit on the pressure forces exerted by said adjustment rod on said measurement shaft and can be controlled by said compensation unit, said normal force measurement unit providing values obtained to said normal force adjustment unit in order to compensate for the pressure forces.

23. The rheometer according to claim 13, further comprising:
a base; and
a rotation drive with which at least one of said DM(T)A analysis device or said adjustment rod can be rotated about an adjustment axis of said adjustment rod relative to said base of the rheometer and can be controlled with said compensation unit functioning as an engine, said compensation unit controlling said rotation drive depending on the torque exerted by said measurement shaft on said adjustment rod in order to compensate for the torque, thus rotating at least one of said linear DM(T)A analysis device or said adjustment rod.

24. The rheometer according to claim 13, wherein a rotational axis of said measurement shaft and a feed axis of said adjustment rod coincide.

25. The rheometer according to claim 13, further comprising a control unit, said compensation unit is one of two compensation units, said compensation unit for said rotation rheometer and said compensation unit for said DM(T)A analysis unit are coupled to said control unit to which a computer and/or analysis unit for readings obtained is connected.

26. The rheometer according to claim 13, wherein:
said rotation rheometer has a base;
said bearing is an air bearing at a specified height over said base of said rotation rheometer;
said further bearing is an air bearing in a specified rotational position; and
the sample is viscoelastic.

* * * * *